US012746062B2

(12) United States Patent
Nageswaran et al.

(10) Patent No.: US 12,746,062 B2
(45) Date of Patent: Sep. 29, 2026

(54) THROMBECTOMY TREATMENT SYSTEM

(71) Applicant: Covidien LP, Mansfield, MA (US)

(72) Inventors: Ashok Nageswaran, Irvine, CA (US); Gaurav Girdhar, Ladera Ranch, CA (US); Hoai Nguyen, Westminster, CA (US); Daniel Deen, Long Beach, CA (US)

(73) Assignee: Covidien LP, Mansfield, MA (US)

( * ) Notice: Subject to any disclaimer, the term of this patent is extended or adjusted under 35 U.S.C. 154(b) by 181 days.

(21) Appl. No.: 18/732,397

(22) Filed: Jun. 3, 2024

(65) Prior Publication Data

US 2024/0315773 A1 Sep. 26, 2024

Related U.S. Application Data

(63) Continuation of application No. 17/249,808, filed on Mar. 15, 2021, now Pat. No. 12,004,803.

(51) Int. Cl.
*A61B 18/14* (2006.01)
*A61B 17/00* (2006.01)
(Continued)

(52) U.S. Cl.
CPC .......... *A61B 18/1492* (2013.01); *A61B 18/16* (2013.01); *A61B 2017/00867* (2013.01); *A61B 2018/00077* (2013.01); *A61B 2018/00083* (2013.01); *A61B 2018/1253* (2013.01); *A61B 2018/126* (2013.01);
(Continued)

(58) Field of Classification Search
CPC ................ A61B 18/1492; A61B 18/16; A61B 2017/00867; A61B 2018/00077; A61B 2018/00083; A61B 2018/1253; A61B 2018/126; A61B 2018/1266; A61B 2218/002; A61B 2218/007
See application file for complete search history.

(56) References Cited

U.S. PATENT DOCUMENTS 5,549,626 A 8/1996 Miller et al.
5,885,278 A 3/1999 Fleischman
(Continued)

FOREIGN PATENT DOCUMENTS

CN 101472685 A 7/2009
CN 102753106 A 10/2012
(Continued)

OTHER PUBLICATIONS

International Search Report and Written Opinion dated Mar. 24, 2022; International Application No. PCT/US2021/061540; 10 pages.
(Continued)

*Primary Examiner* — Linda C Dvorak
*Assistant Examiner* — Abigail Bock
(74) *Attorney, Agent, or Firm* — Fortem IP LLP

(57) ABSTRACT

A medical treatment device is disclosed herein. In one example, the medical treatment device includes a core assembly which has a first conduct and a second conductor. An insulative material can surround the second conductor and define an electrode portion of the second conductor that is uncovered by the insulative material. The medical treatment device can include an interventional element that electrical couples to the first conductor. The electrode portion of the second conductor can be disposed radially adjacent to or distal of the interventional element.

20 Claims, 8 Drawing Sheets

(51) Int. Cl.
*A61B 18/00* (2006.01)
*A61B 18/12* (2006.01)
*A61B 18/16* (2006.01)

(52) U.S. Cl.
CPC . *A61B 2018/1266* (2013.01); *A61B 2218/002* (2013.01); *A61B 2218/007* (2013.01)

(56) References Cited

U.S. PATENT DOCUMENTS 5,928,260 A 7/1999 Chin et al.
5,972,019 A 10/1999 Engelson et al.
6,022,336 A 2/2000 Zadno-Azizi et al.
6,059,779 A 5/2000 Mills
6,183,467 B1 2/2001 Shapeton et al.
6,315,794 B1 11/2001 Richter
6,540,733 B2 4/2003 Constantz et al.
6,658,288 B1 12/2003 Hayashi
6,663,650 B2 12/2003 Sepetka et al.
6,922,579 B2 7/2005 Taimisto et al.
7,094,249 B1 8/2006 Broome et al.
7,520,966 B2 4/2009 Diaz et al.
7,556,624 B2 7/2009 Laufer et al.
7,742,795 B2 6/2010 Stone et al.
8,032,222 B2 10/2011 Loushin et al.
8,038,674 B2 10/2011 Schmaltz et al.
8,246,641 B2 8/2012 Osborne et al.
8,382,821 B2 2/2013 Richter
8,603,014 B2 12/2013 Alleman et al.
8,795,305 B2 8/2014 Martin et al.
8,837,800 B1 9/2014 Bammer et al.
8,888,788 B2 11/2014 Adams et al.
8,965,534 B2 2/2015 Hyatt et al.
9,011,431 B2 4/2015 Long et al.
9,039,753 B2 5/2015 Thramann
9,119,656 B2 9/2015 Bose et al.
9,126,018 B1 9/2015 Garrison
9,179,971 B2 11/2015 Kirschenman
9,211,132 B2 12/2015 Bowman
9,241,699 B1 1/2016 Kume et al.
9,265,512 B2 2/2016 Garrison et al.
9,308,007 B2 4/2016 Cully et al.
9,399,118 B2 7/2016 Kume et al.
9,445,828 B2 9/2016 Turjman et al.
9,445,829 B2 9/2016 Brady et al.
9,492,637 B2 11/2016 Garrison et al.
9,539,022 B2 1/2017 Bowman
9,561,345 B2 2/2017 Garrison et al.
9,579,119 B2 2/2017 Cully et al.
9,585,741 B2 3/2017 Ma
9,642,635 B2 5/2017 Vale et al.
9,655,633 B2 5/2017 Leynov et al.
9,681,882 B2 6/2017 Wilson et al.
9,713,730 B2 7/2017 Mathur et al.
9,737,318 B2 8/2017 Monstadt et al.
9,770,251 B2 9/2017 Bowman et al.
9,795,400 B2 10/2017 Davidson
9,801,643 B2 10/2017 Hansen et al.
9,808,271 B2 11/2017 Ulm
9,827,084 B2 11/2017 Bonnette et al.
9,861,783 B2 1/2018 Garrison et al.
9,901,543 B2 2/2018 Chausson et al.
9,993,257 B2 6/2018 Losordo et al.
10,028,782 B2 7/2018 Orion
10,029,008 B2 7/2018 Creighton
10,039,906 B2 8/2018 Kume et al.
10,092,241 B2 10/2018 Toth et al.
10,136,942 B1 11/2018 Cosman
10,251,569 B2 4/2019 Burkett
10,413,309 B2 9/2019 Farhat et al.
10,709,463 B2 7/2020 Girdhar et al.
10,847,411 B2 11/2020 Chen et al.
10,874,411 B2 12/2020 Nguyen et al.
10,987,117 B2 4/2021 Girdhar et al.
11,058,444 B2 7/2021 Girdhar et al.
11,090,071 B2 8/2021 Girdhar et al.
11,160,571 B2 11/2021 Nguyen et al.
11,666,350 B2 6/2023 Nguyen et al.
11,832,836 B2 12/2023 Girdhar et al.
11,944,332 B2 4/2024 Girdhar et al.
11,944,334 B2 4/2024 Girdhar et al.
11,944,374 B2 4/2024 Girdhar et al.
11,950,794 B2 4/2024 Nguyen et al.
11,963,713 B2 4/2024 Girdhar et al.
2001/0001314 A1 5/2001 Davison et al.
2002/0059938 A1 5/2002 Fogarty et al.
2002/0091407 A1 7/2002 Zadno-Azizi et al.
2002/0133111 A1 9/2002 Shadduck et al.
2003/0088245 A1 5/2003 Woloszko et al.
2004/0073243 A1 4/2004 Sepetka et al.
2004/0219660 A1 11/2004 Dev et al.
2005/0096647 A1 5/2005 Steinke et al.
2005/0228417 A1 10/2005 Teitelbaum et al.
2006/0089638 A1 4/2006 Carmel et al.
2008/0042662 A1 2/2008 Abraham
2008/0045881 A1 2/2008 Teitelbaum et al.
2008/0262489 A1 10/2008 Steinke et al.
2008/0294181 A1 11/2008 Wensel et al.
2008/0300571 A1 12/2008 Lepivert
2009/0024154 A1 1/2009 Williams et al.
2009/0054918 A1 2/2009 Henson
2009/0069828 A1 3/2009 Martin et al.
2009/0240250 A1 9/2009 Hayashi et al.
2009/0318892 A1 12/2009 Aboytes et al.
2009/0318943 A1 12/2009 Eidenschink et al.
2009/0318994 A1 12/2009 Eidenschink et al.
2010/0004623 A1 1/2010 Hamilton et al.
2010/0010533 A1 1/2010 Burke et al.
2010/0042136 A1 2/2010 Berrada et al.
2010/0168739 A1 7/2010 Wu et al.
2010/0174309 A1 7/2010 Fulkerson et al.
2010/0228280 A1 9/2010 Groothuis et al.
2010/0256616 A1 10/2010 Katoh et al.
2010/0256627 A1 10/2010 Ma et al.
2011/0130756 A1 6/2011 Everson et al.
2011/0196478 A1 8/2011 Torosoff
2011/0202085 A1 8/2011 Loganathan et al.
2011/0301506 A1 12/2011 Volz
2011/0301549 A1 12/2011 Hartmann
2011/0301594 A1 12/2011 Orion et al.
2013/0008780 A1 1/2013 Andreacchi et al.
2013/0030461 A1 1/2013 Marks et al.
2013/0072960 A1 3/2013 Schneider et al.
2013/0184702 A1 7/2013 Neal et al.
2013/0237864 A1 9/2013 Mazar et al.
2013/0281788 A1 10/2013 Garrison
2013/0282084 A1 10/2013 Mathur et al.
2013/0345739 A1 12/2013 Brady et al.
2014/0025069 A1 1/2014 Willard et al.
2014/0025152 A1 1/2014 Headley
2014/0172001 A1 6/2014 Becking et al.
2014/0180139 A1 6/2014 Millett et al.
2014/0188127 A1 7/2014 Dubrul et al.
2014/0243882 A1 8/2014 Ma
2014/0265030 A1 9/2014 Janardhan et al.
2014/0276074 A1 9/2014 Warner
2014/0276778 A1 9/2014 McLawhorn et al.
2014/0277013 A1 9/2014 Sepetka et al.
2014/0277079 A1 9/2014 Vale et al.
2014/0309673 A1 10/2014 Dacuycuy et al.
2014/0309675 A1 10/2014 Maisano et al.
2014/0343595 A1 11/2014 Monstadt et al.
2014/0364896 A1 12/2014 Consigny
2015/0112321 A1 4/2015 Cadouri
2015/0133990 A1 5/2015 Davidson
2015/0150672 A1 6/2015 Ma
2015/0164666 A1 6/2015 Johnson et al.
2015/0182740 A1 7/2015 Mickelsen
2015/0230820 A1 8/2015 Turjman et al.
2015/0297251 A1 10/2015 Sos
2015/0359547 A1 12/2015 Vale et al.
2016/0008003 A1 1/2016 Kleshinski et al.
2016/0015402 A1 1/2016 Brady et al.
2016/0015935 A1 1/2016 Chan et al.
2016/0106448 A1 4/2016 Brady et al.

(56) References Cited

U.S. PATENT DOCUMENTS

| | | | |
|---|---|---|---|
| 2016/0106449 | A1 | 4/2016 | Brady et al. |
| 2016/0113663 | A1 | 4/2016 | Brady et al. |
| 2016/0113665 | A1 | 4/2016 | Brady et al. |
| 2016/0151618 | A1 | 6/2016 | Powers et al. |
| 2016/0157843 | A1 | 6/2016 | Dickson et al. |
| 2016/0157985 | A1 | 6/2016 | Vo et al. |
| 2016/0199620 | A1 | 7/2016 | Pokorney et al. |
| 2016/0228681 | A1 | 8/2016 | Di Palma et al. |
| 2016/0228684 | A1 | 8/2016 | Martin |
| 2016/0242661 | A1 | 8/2016 | Fischell et al. |
| 2016/0296690 | A1 | 10/2016 | Kume et al. |
| 2016/0302808 | A1 | 10/2016 | Loganathan et al. |
| 2016/0331377 | A1 | 11/2016 | Divino et al. |
| 2016/0375180 | A1 | 12/2016 | Anzai |
| 2017/0079766 | A1 | 3/2017 | Wang et al. |
| 2017/0079767 | A1 | 3/2017 | Leon-Yip |
| 2017/0086862 | A1 | 3/2017 | Vale et al. |
| 2017/0100143 | A1 | 4/2017 | Grandfield |
| 2017/0105743 | A1 | 4/2017 | Vale et al. |
| 2017/0128126 | A1 | 5/2017 | Sunenshine et al. |
| 2017/0164963 | A1 | 6/2017 | Goyal |
| 2017/0172644 | A1 | 6/2017 | Butzbacker et al. |
| 2017/0215902 | A1 | 8/2017 | Leynov et al. |
| 2017/0215955 | A1 | 8/2017 | Hancock et al. |
| 2017/0224953 | A1 | 8/2017 | Tran et al. |
| 2017/0281909 | A1 | 10/2017 | Northrop et al. |
| 2017/0290599 | A1 | 10/2017 | Youn et al. |
| 2017/0367707 | A1 | 12/2017 | Divino |
| 2018/0049762 | A1 | 2/2018 | Seip et al. |
| 2018/0084982 | A1 | 3/2018 | Yamashita et al. |
| 2018/0116685 | A1 | 5/2018 | Ulm |
| 2018/0116717 | A1 | 5/2018 | Taff et al. |
| 2018/0132876 | A1 | 5/2018 | Zaidat |
| 2018/0133436 | A1 | 5/2018 | Garrison et al. |
| 2018/0140314 | A1 | 5/2018 | Goyal et al. |
| 2018/0140315 | A1 | 5/2018 | Bowman et al. |
| 2018/0140354 | A1 | 5/2018 | Lam et al. |
| 2018/0161514 | A1 | 6/2018 | Rothenberg et al. |
| 2018/0161541 | A1 | 6/2018 | Haldis et al. |
| 2018/0185614 | A1 | 7/2018 | Garrison et al. |
| 2018/0193026 | A1 | 7/2018 | Yang et al. |
| 2018/0200040 | A1 | 7/2018 | Wasdyke et al. |
| 2018/0236221 | A1 | 8/2018 | Opie et al. |
| 2018/0303595 | A1 | 10/2018 | Opie et al. |
| 2018/0344970 | A1 | 12/2018 | Kornowski et al. |
| 2019/0038438 | A1 | 2/2019 | John et al. |
| 2019/0046119 | A1 | 2/2019 | Oxley |
| 2019/0175199 | A1 | 6/2019 | Girdhar et al. |
| 2019/0175200 | A1 | 6/2019 | Girdhar et al. |
| 2019/0239910 | A1 | 8/2019 | Brady et al. |
| 2019/0262069 | A1 | 8/2019 | Taff et al. |
| 2019/0336727 | A1 | 11/2019 | Yang et al. |
| 2019/0388097 | A1 | 12/2019 | Girdhar et al. |
| 2019/0388107 | A1 | 12/2019 | Girdhar et al. |
| 2019/0388111 | A1 | 12/2019 | Nguyen et al. |
| 2019/0388112 | A1 | 12/2019 | Nguyen et al. |
| 2020/0054392 | A1 | 2/2020 | Whiteley et al. |
| 2020/0129742 | A1 | 4/2020 | Cope et al. |
| 2020/0297367 | A1 | 9/2020 | Girdhar et al. |
| 2020/0297410 | A1 | 9/2020 | Nguyen et al. |
| 2020/0390455 | A1 | 12/2020 | Nguyen et al. |
| 2020/0390456 | A1 | 12/2020 | Nguyen et al. |
| 2020/0390457 | A1 | 12/2020 | Nageswaran et al. |
| 2020/0390458 | A1 | 12/2020 | Nguyen et al. |
| 2021/0068853 | A1 | 3/2021 | Nguyen et al. |
| 2021/0137542 | A1 | 5/2021 | Oxley et al. |
| 2021/0177427 | A1 | 6/2021 | Nguyen et al. |
| 2021/0177442 | A1 | 6/2021 | Girdhar et al. |
| 2021/0177446 | A1 | 6/2021 | Girdhar et al. |
| 2021/0186540 | A1 | 6/2021 | Taff et al. |
| 2021/0238764 | A1 | 8/2021 | Tyvoll et al. |
| 2021/0267612 | A1 | 9/2021 | Girdhar et al. |
| 2021/0272676 | A1 | 9/2021 | Dierl |
| 2022/0022899 | A1 | 1/2022 | Girdhar et al. |
| 2022/0022900 | A1 | 1/2022 | Nguyen et al. |
| 2022/0125455 | A1 | 4/2022 | Girdhar et al. |
| 2022/0202431 | A1 | 6/2022 | Davidson et al. |
| 2022/0218372 | A1 | 7/2022 | Nguyen et al. |
| 2022/0236569 | A1 | 7/2022 | Yamazaki et al. |
| 2022/0287765 | A1 | 9/2022 | Nageswaran et al. |
| 2022/0313288 | A1 | 10/2022 | Janardhan et al. |
| 2022/0387051 | A1 | 12/2022 | Girdhar et al. |
| 2022/0387098 | A1 | 12/2022 | Girdhar et al. |
| 2022/0409258 | A1 | 12/2022 | Girdhar et al. |
| 2023/0064470 | A1 | 3/2023 | Girdhar et al. |
| 2023/0277240 | A1 | 9/2023 | Wu et al. |
| 2024/0074772 | A1 | 3/2024 | Girdhar et al. |

FOREIGN PATENT DOCUMENTS

| | | | |
|---|---|---|---|
| CN | 104994799 | A | 10/2015 |
| CN | 107405160 | A | 11/2017 |
| CN | 104884681 | B | 5/2018 |
| EP | 1484025 | A1 | 12/2004 |
| EP | 2319575 | B1 | 11/2013 |
| EP | 2490764 | B1 | 9/2014 |
| EP | 2895645 | A1 | 7/2015 |
| EP | 2967605 | A1 | 1/2016 |
| EP | 3184067 | A1 | 6/2017 |
| JP | 10290805 | A | 11/1998 |
| JP | 2014004219 | A | 1/2014 |
| JP | 2018118132 | A | 8/2018 |
| KR | 20180102877 | A | 9/2018 |
| WO | 9724073 | A1 | 7/1997 |
| WO | 0035363 | A1 | 6/2000 |
| WO | 2005000130 | A1 | 1/2005 |
| WO | 2009127037 | A1 | 10/2009 |
| WO | 2010061376 | A1 | 6/2010 |
| WO | 2014079148 | A1 | 5/2014 |
| WO | 2014168750 | A1 | 10/2014 |
| WO | 2015141317 | A1 | 9/2015 |
| WO | 2016007388 | A1 | 1/2016 |
| WO | 2016141025 | A1 | 9/2016 |
| WO | 2016198947 | A1 | 12/2016 |
| WO | 2017058696 | A1 | 4/2017 |
| WO | 2017192999 | A1 | 11/2017 |
| WO | 2018019829 | A1 | 2/2018 |
| WO | 2018033401 | A1 | 2/2018 |
| WO | 2018046408 | A2 | 3/2018 |
| WO | 2018127796 | A1 | 7/2018 |
| WO | 2018137029 | A1 | 8/2018 |
| WO | 2018137030 | A1 | 8/2018 |
| WO | 2018145212 | A1 | 8/2018 |
| WO | 2018156813 | A1 | 8/2018 |
| WO | 2018172891 | A1 | 9/2018 |
| WO | 2018187776 | A1 | 10/2018 |
| WO | 2019102307 | A1 | 5/2019 |
| WO | 2019118321 | A1 | 6/2019 |
| WO | 2019133608 | A1 | 7/2019 |
| WO | 2019246377 | A2 | 12/2019 |
| WO | 2020174326 | A1 | 9/2020 |

OTHER PUBLICATIONS

International Search Report and Written Opinion mailed Aug. 19, 2022, International Application No. PCT/US2022/031799, 12 pages.
International Search Report and Written Opinion mailed Feb. 26, 2021; International Application No. PCT/US20/63200; 14 pages.
International Search Report and Written Opinion mailed May 25, 2020, International Application No. PCT/US20/22463, 10 pages.
International Search Report and Written Opinion mailed Nov. 3, 2020, International Application No. PCT/US20/70142, 18 pages.
Chon, CH , et al., "Mechanical behavior of rf-treated thrombus in mechanical thrombectomy", Qin Z, Kwok JC, Lam DC; Med Eng Phys. Sep. 2017;47:184-189. doi: 10.1016/j.medengphy.2017.06.011. Epub Jul. 5, 2017. PMID: 28688756. (Year: 2017).
Fort , et al., "'Fused-Gold' vs. 'Bare' stainless steel NIRflex stents of the same geometric design in diseased native coronary arteries. Long-term results from the NIR TOP Study", EuroIntervention, vol. 3, May 22, 2007, pp. 256-261.

THROMBECTOMY TREATMENT SYSTEM

CROSS-REFERENCE TO RELATED APPLICATION(S)

The present application is a continuation of U.S. patent application Ser. No. 17/249,808, filed Mar. 15, 2021 which is incorporated by reference herein in its entirety.

TECHNICAL FIELD

The present technology relates to relates generally to devices, systems, and methods for removing obstructions from body lumens. Some embodiments of the present technology relate to devices and methods for delivering electrical current within a medical treatment system.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (e.g., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. The treatment systems of the present technology provide an interventional element and a current generator configured to positively charge the interventional element during one or more stages of a thrombectomy procedure. For example, the current generator may apply a constant or pulsatile direct current (DC) to the interventional element. The positively charged interventional element attracts negatively charged blood components, thereby improving attachment of the thrombus to the interventional element and reducing the number of device passes or attempts necessary to fully retrieve the clot. In some aspects of the present technology, the treatment system includes an elongate core assembly (e.g., a cable) extending between the current generator and the interventional element. A delivery electrode may be integrated into the core assembly and/or interventional element, and the treatment system further includes a negative electrode that may be disposed at a number of different locations. For example, the negative electrode can be a wire coupled to or integrated within the core assembly. Additionally or alternatively, a negative electrode can take the form of a needle, a grounding pad, a conductive element carried by a one or more catheters of the treatment system, a separate guide wire, and/or any other suitable conductive element configured to complete an electrical circuit with the delivery electrode and the extracorporeally positioned current generator. When the interventional element is placed in the presence of blood (or any other electrolytic medium) and voltage is applied at the terminals of the current generator, current flows along the core assembly to the interventional element, through the blood, and to the return electrode, thereby positively charging at least a portion of the interventional element and adhering clot material thereto.

One approach to delivering current to an interventional element is to conduct current along a core member coupled to a proximal end of the interventional element. However, the inventors have discovered that this approach can lead to disadvantageous concentration of electrical charge along a proximal portion of the interventional element, with insufficient charge density in more distal portions of the interventional element (e.g., along some or all of the working length of the interventional element). This is particularly true of an interventional element having a proximal portion that tapers to a connection point with the core member. This concentration of current in the proximal portion can reduce the efficacy of electrostatic enhancement of clot adhesion, as the mechanical clot engagement occurs primarily at a location distal to the region at which the charge density is greatest. Additionally, when used in an aqueous chloride environment, such as the blood, hydrogen and chlorine gas bubbles can form along the surface of the interventional element in areas with high surface charge density (e.g., along a proximal portion of the interventional element). To reduce risk to the patient and ensure the treatment system functions properly, it may be beneficial to ensure that current flows through the entire interventional element, particularly ensuring sufficient current density in distal portions of the interventional element. When the entire interventional element exhibits a positive electrical charge, all portions of the interventional element can attract negatively charged blood components, thereby improving attachment of the thrombus to the interventional element. If portions of the interventional element are not positively charged (e.g., the distal portion is electrically neutral or exhibits insufficient charge density), those portions of the interventional element may not adequately attract negatively charged blood components, which can prevent improved attachment of the thrombus to the interventional element.

Embodiments of the present technology address these and other problems by providing a core assembly that positions negative electrode(s) relative to the interventional element at locations that facilitate current distribution across the interventional element. For example, to encourage current to flow through all portions of the interventional element, the negative electrode can be positioned at or distal to the interventional element in a manner that encourages current to flow through all portions of the interventional element. In some embodiments, the core assembly can take the form of an elongated conductor such as a wire, with an insulation material surrounding the wire along its length. The insulation material can include gaps or apertures along a distal region of the wire that define negative electrode(s). These uninsulated sections can be located at specific locations that encourage current to flow through the entire interventional element. For example, one or more negative electrodes can be located proximate the distal end of the interventional element, which encourages current to flow to the distal end of the interventional element. By positioning one or more electrode portions at advantageous locations, the interventional element can reliably maintain a positive charge during treatment.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings. The subject technology is illustrated, for example, according to various aspects described below. Various examples of aspects of the subject technology are described as numbered clauses (1, 2, 3, etc.) for convenience. These are provided as examples and do not limit the subject technology.

1. A medical device comprising:
 a core assembly configured to be advanced within a lumen of a corporeal lumen, the core assembly comprising:
  a first conductor having a proximal end portion and a distal end portion, the first conductor forming a lumen;
  a second conductor at least partially disposed within the lumen of the first conductor, the second conductor having a proximal end portion and a distal end portion; and
  an insulative material surrounding the second conductor along at least a part of its length, the insulative material defining an electrode portion of the second conductor that is uncovered by the insulative material; and
 an interventional element coupled to the distal end portion of the first conductor, the interventional element electrically coupled to the first conductor,
 wherein the electrode portion of the second conductor is disposed radially adjacent to or distal of the interventional element.
2. The medical device of Clause 1, wherein the first and second conductors are coaxial.
3. The medical device of Clause 1 or 2, wherein the core assembly comprises a distally located joining element having an opening therein, and wherein the second conductor extends through the opening.
4. The medical device of any one of Clauses 1 to 3, wherein the interventional element defines a lumen, and wherein the second conductor extends at least partially through the lumen.
5. The medical device of Clause 4, wherein the electrode portion of the second conductor is disposed within the lumen.
6. The medical device of Clause 4 or 5, wherein the first conductor and the second conductor are non-slidably coupled together.
7. The medical device of any one of Clauses 1 to 6, further comprising a current generator electrically coupled to the first and second conductors,
8. The medical device of Clause 7, wherein the current generator is configured to supply an electrical current to one or both of the first and second conductors.
9. The medical device of any one of Clauses 1 to 8, wherein the electrode portion comprises a spiral opening in the insulative material.
10. The medical device of any one of Clauses 1 to 9, wherein the electrode portion comprises a plurality of openings in the insulative material, the openings being spaced apart along the length of the electrode portion.
11. The medical device of Clause 10, wherein the plurality of openings are located at substantially the same angular position about a longitudinal axis of the second conductor.

12. The medical device of any one of Clauses 1 to 11, wherein the electrode portion comprises an uninsulated portion at the distal end portion of the second conductor.
13. The medical device of any one of Clauses 1 to 12, wherein the electrode portion comprises a plurality of annular openings in the insulative material, the annular openings being spaced apart along the length of the electrode portion.
14. The medical device of any one of Clauses 1 to 13, wherein the electrode portion is positioned distal to a distal end of the interventional element.
15. The medical device of any one of Clauses 1 to 14, wherein the electrode portion is spaced apart from a distal terminus of the second conductor by a portion of the insulative material.
16. The medical device of any one of Clauses 1 to 15, wherein the first conductor comprises a hypotube.
17. The medical device of any one of Clauses 1 to 16, wherein the core assembly is sized and configured to be advanced through a blood vessel to a treatment site.
18. The medical device of any one of Clauses 1 to 17, wherein the distal end portion of the second conductor is positioned distal of the distal end portion of the first conductor.
19. The medical device of any one of Clauses 1 to 18, wherein the electrode portion of the second conductor comprises a first material, wherein the interventional element comprises a second material disposed an outer surface of the interventional element, and wherein the first material is the same as the second material.
20. The medical device of any one of Clauses 1 to 19, wherein the interventional element comprises an electrode surface having a first material, wherein the electrode portion of the second conductor comprises a second material, and wherein the first material is the same as the second material.
21. The medical device of any one of Clauses 1 to 20, wherein the interventional element comprises an expandable mesh.
22. The medical device of any one of Clauses 1 to 21, wherein the interventional element comprises a stent retriever.
23. The medical device of any one of Clauses 1 to 22, wherein the interventional element comprises a plurality of struts that are bounded to form a cell opening, the electrode portion of the second conductor being positioned radially adjacent to the cell opening.
24. The medical device of any one of Clauses 1 to 23, wherein the electrode portion of the second conductor is configured to be oriented to face radially away from a portion of the interventional element that is nearest the second conductor.
25. The medical device of any one of Clauses 1 to 24, wherein the interventional element comprises a plurality of struts, the electrode portion of the second conductor being oriented to face away from the plurality of struts.
26. A medical device comprising:
an elongated shaft having a proximal portion configured to be electrically coupled to a terminal of a current generator, an intermediate portion covered with an insulative material, and a distal portion defining an electrode portion;
an elongated tubular member having a proximal portion configured to be electrically coupled to a current generator, a distal portion, and a lumen receiving the elongated shaft therethrough; and
an interventional element coupled to the distal portion of the elongated tubular member, the interventional element at least partially surrounding the distal portion of the elongated shaft.
27. The medical device of Clause 26, wherein the interventional element is electrically coupled to the elongated tubular member.
28. The medical device of Clause 26 or 27, wherein the electrode portion comprises an uninsulated portion of the elongated shaft.
29. The medical device of any one of Clauses 26 to 28, wherein the elongated tubular member and the elongated shaft are non-slidably coupled together.
30. The medical device of any one of Clauses 26 to 29, wherein the interventional element comprises an expandable mesh.
31. The medical device of any one of Clauses 26 to 30, wherein the interventional element comprises a stent retriever.
32. The medical device of any one of Clauses 26 to 31, wherein the elongated shaft and the elongated tubular member are coaxial.
33 The medical device of any one of Clauses 26 to 32, wherein the elongated tubular member comprises a distally located joining element having an opening therein, wherein the elongated shaft extends through the opening, and wherein the interventional element comprises a proximally located attachment element that extends through the opening.
34. The medical device of Clause 33, wherein the proximally located attachment element interlocks with the distally located joining element, and wherein the elongated shaft retains the proximally located attachment element within the opening.
35. The medical device of any one of Clauses 26 to 34, wherein the electrode portion comprises a plurality of electrodes.
36. A medical device comprising:
a first conductor having a proximal end portion and a distal end portion configured to be positioned proximate a thrombus within a lumen of a blood vessel at a treatment site;
an interventional element coupled to the first conductor, the first conductor configured to convey electrical current to the interventional element;
a second conductor having a proximal end portion and a distal end portion, at least a part of the distal end portion of the second conductor extending through the interventional element; and
an insulative material disposed over the second conductor, the insulative material configured to electrically insulate the second conductor, the insulative material defining an electrode portion on the second conductor, the second conductor and the plurality of electrode portions being configured to provide a return path for an electrical current from the interventional element.
37. The medical device of Clause 36, wherein the first and second conductors are coaxial.
38. The medical device of Clause 36 or 37, wherein the first conductor forms a lumen, and wherein at least a part of the second conductor is disposed within the lumen.
39. The medical device of any one of Clause 36 to 38, wherein the first conductor comprises a distally located joining element having an opening therein, wherein the second conductor extends through the opening, and wherein the interventional element comprises a proximally located attachment element that extends through the opening.

40. The medical device of Clause 39, wherein the proximally located attachment element interlocks with the distally located joining element, and wherein the second conductor retains the proximally located attachment element within the opening.

41. The medical device of any one of Clauses 36 to 40, wherein the interventional element defines a lumen, and wherein the second conductor extends at least partially through the lumen.

42. The medical device of Clause 41, wherein the electrode portion is disposed within the lumen.

43. The medical device of Clause 41 or 42, wherein the first conductor and the second conductor are non-slidably coupled together.

44. The medical device of any one of Clauses 36 to 43, further comprising a current generator coupled to the proximal end portions of the first and second conductor, the current generator being configured to supply the electrical current to the first and second conductors.

45. The medical device of any one of Clauses 36 to 44, further comprising a plurality of electrode portions, wherein the plurality of electrode portions comprises a spiral opening in the insulative material.

46. The medical device of any one of Clauses 36 to 45, further comprising a plurality of electrode portions, wherein the plurality of electrode portions comprises a plurality of openings in the insulative material, the openings being spaced apart along the length of the electrode portion.

47. The medical device of any one of Clauses 36 to 46, further comprising a plurality of electrode portions, wherein the plurality of electrode portions comprises an uninsulated portion at the distal end portion of the second conductor.

48. The medical device of any one of Clauses 36 to 47, further comprising a plurality of electrode portions, wherein the plurality of electrode portions comprises a plurality of annular openings in the insulative material, the annular openings being spaced apart along the length of the electrode portion.

49. The medical device of any one of Clauses 36 to 48, wherein at least some of the electrode portion extends through the interventional element.

50. The medical device of any one of Clauses 36 to 49, wherein the first conductor comprises a hypotube.

51. The medical device of any one of Clauses 36 to 50, wherein the core assembly is sized and configured to be advanced through a corporeal lumen to the treatment site.

52. The medical device of any one of Clauses 36 to 51, wherein the insulative material defines a plurality of electrode portions along the second conductor.

53. A method for delivering an electrical current to a treatment device, the method comprising:

inserting a treatment device into a patient, the treatment device comprising:

a core assembly comprising:

a first conductor having a proximal end portion and a distal end portion, the first conductor forming a lumen;

a second conductor at least partially disposed within the lumen of the first conductor, the second conductor having a proximal end portion and a distal end portion; and an insulative material coupled to the second conductor and defining an electrode portion of the second conductor; and an interventional element coupled to the distal end portion of the first conductor of the core assembly, the interventional element electrically coupled to the first conductor;

positioning the treatment device proximate a thrombus within a lumen of a blood vessel at a treatment site; and delivering an electrical current to the treatment device.

54. The method of Clause 53, further comprising ceasing delivery of the electrical current to the treatment device after a time period.

55. The method of Clause 54, wherein the time period is two minutes or less.

56. The method of any one of Clauses 53 to 55, wherein delivering the electrical current positively charges the interventional element.

57. The method of any one of Clauses 53 to 56, further comprising expanding the interventional element into engagement with the thrombus.

58. The method of any one of Clauses 53 to 57, wherein at least a part of the electrode portion of the second conductor extends through the interventional element.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments, in addition to those described herein, are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.). In some embodiments, aspects of the present technology can be applied to medical devices and systems that are not configured for removal of material from vessel lumens, for example systems and devices for ablation, neuromodulation, or any other suitable medical procedure.

Figure 1A:
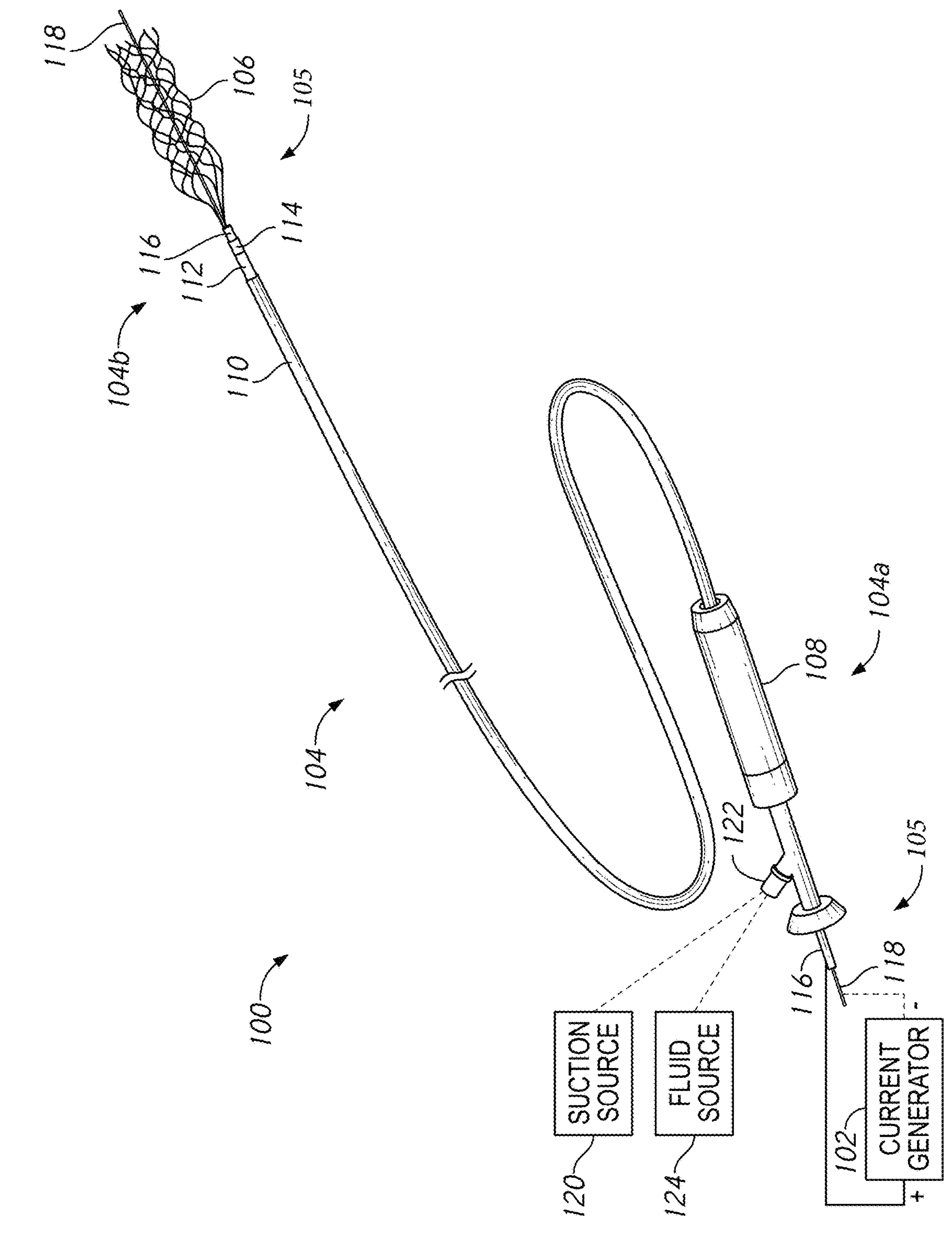
FIG. 1A shows a perspective view of an electrically enhanced treatment system for retrieving material from a body lumen, in accordance with one or more embodiments of the present technology.

FIG. 1A illustrates a view of an electrically enhanced treatment system 100 according to one or more embodiments of the present technology. As shown in FIG. 1A, the treatment system 100 can include a current generator 102 and a treatment device 104 having a proximal portion 104*a* configured to be coupled to the current generator 102 and a distal portion 104*b* configured to be intravascularly positioned within a blood vessel (such as an intracranial blood vessel) at a treatment site at or proximate a thrombus. The treatment device 104 includes an interventional element 106 at the distal portion 104*b*, a handle 108 at the proximal portion 104*a*, and a plurality of elongated shafts or members extending therebetween. For example, in some embodiments, such as that shown in FIG. 1A, the treatment device 104 includes a first catheter 110 (such as a guide catheter or balloon guide catheter), a second catheter 112 (such as a distal access catheter or aspiration catheter) configured to be slidably disposed within a lumen of the first catheter 110, and a third catheter 114 (such as a microcatheter) configured to be slidably disposed within a lumen of the second catheter 112. In some embodiments, the treatment device 104 can include a core assembly 105 extending between the proximal portion 104*a* and distal portion 104*b* of the treatment device 104. In some embodiments, the treatment device 104 does not include the first catheter 110 and/or the second catheter 112.

The core assembly 105 is configured to be slidably disposed within the lumen of the third catheter 114. In the illustrated embodiment, the core assembly 105 can take the form of an electrical cable or other such assembly that includes a first electrical conductor 116 and a second electrical conductor 118. As discussed in more detail below, in some instances the first conductor 116 can take the form of an elongated tube (e.g., a hypotube) made of or including an electrically conductive material, and the second conductor 118 can take the form of an elongated wire or rod that is made of or includes an electrically conductive material. In some embodiments, the second conductor 118 is configured to be disposed within a lumen of the first conductor 116. In some embodiments, the first conductor 116 and second conductor 118 are coaxial. In various embodiments, the first conductor 116 and second conductor 118 are non-slidably coupled together. The first conductor 116 and second conductor 118 can be sized and configured to be advanced through a corporeal lumen to the treatment site. For example, the first conductor 116 and second conductor 118 can be sized to be positioned proximate a thrombus within a lumen of a blood vessel, such as within a patient's neurovasculature. The first conductor 116 and/or the second conductor 118 can be electrically insulated along at least a portion of their respective lengths. In some embodiments, the first catheter 110 can be coupled to (or incorporate) the handle 108, which provides proximal access to the first conductor 116 and second conductor 118.

The current generator 102 may be coupled to the core assembly 105 to deliver electrical current to the interventional element 106 and thereby provide an electrically charged environment at the distal portion 104*b* of the treatment device 104. Further, the current generator 102 may be coupled to the core assembly 105 to return electrical current from the electrically charged environment to the current generator 102. In various embodiments, the current generator 102 can be electrically coupled to the first conductor 116, the second conductor 118, or both.

In some embodiments, the treatment system 100 includes a suction source 120 (e.g., a syringe, a pump, etc.) configured to be fluidically coupled (e.g., via a connector 122) to a proximal portion of one or more of the first catheter 110, the second catheter 112, and/or the third catheter 114 to apply negative pressure therethrough. In some embodiments, the treatment system 100 includes a fluid source 124 (e.g., a fluid reservoir, a syringe, pump, etc.) configured to be fluidically coupled (e.g., via the connector 122) to a proximal portion of one or more of the first catheter 110, the second catheter 112, and/or the third catheter 114 to supply fluid (e.g., saline, contrast agents, a drug such as a thrombolytic agent, etc.) to the treatment site.

According to some embodiments, the catheters 110, 112, and 114 can each be formed as a generally tubular member extending along and about a central axis. According to some embodiments, the third catheter 114 is generally constructed to track over a conventional guidewire in the cervical anatomy and into the cerebral vessels associated with the brain and may also be chosen according to several standard designs that are generally available. Accordingly, the third catheter 114 can have a length that is at least 125 cm long, and more particularly may be between about 125 cm and about 175 cm long. Other designs and dimensions are contemplated.

The second catheter 112 can be sized and configured to slidably receive the third catheter 114 therethrough. As noted above, the second catheter 112 can be coupled at a proximal portion to a suction source 120 (FIG. 1A) such as a pump or syringe in order to supply negative pressure to a treatment site. The first catheter 110 can be sized and configured to slidably receive both the second catheter 112 and the third catheter 114 therethrough. In some embodiments, the first catheter 110 is a balloon guide catheter having an inflatable balloon or other expandable member surrounding the catheter shaft at or near its distal end. In operation the first catheter 110 can first be advanced through a vessel and then its balloon can be expanded to anchor the first catheter 110 in place and/or arrest blood flow from areas proximal of the balloon, e.g. to enhance the effectiveness of aspiration performed via the first catheter 110 and/or other catheter(s). Alternatively, a guide catheter without a balloon can be employed. Next, the second catheter 112 can be advanced through the first catheter 110 until its distal end extends distally beyond the distal end of the first catheter 110. The second catheter 112 can be positioned such that its distal end is adjacent or proximal of a treatment site (e.g., a site of a blood clot within the vessel). The third catheter 114 may then be advanced through the second catheter 112 until its distal end extends distally beyond the distal end of the second catheter 112. The interventional element 106 may then be advanced through the third catheter 114 via the core assembly 105 for delivery to the treatment site.

According to some embodiments, the bodies of the catheters 110, 112, and 114 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

In some embodiments, the current generator 102 may be coupled to a proximal portion of the first conductor 116, and/or a proximal portion of the third catheter 114, the second catheter 112, and/or first catheter 110 to provide an electric current to the interventional element 106. For example, as shown in FIG. 1A, the current generator 102 can be coupled to a proximal portion of the core assembly 105 and/or the first conductor 116 such that the first conductor 116 functions as a first conductive path (e.g., as a positive conductive path transmitting current from the current generator to the treatment site). As shown in FIG. 1A, the current generator 102 can also be coupled to a proximal portion of the second conductor 118 such that the second conductor 118 functions as a second conductive path (e.g., as a negative conductive path transmitting current from the treatment site to the current generator 102). In other embodiments, the negative electrode can be separate from the second conductor 118. In some embodiments, the positive electrode can comprise the interventional element 106, and the negative electrode can be carried by one or more of the third catheter 114, the second catheter 112, and/or first catheter 110, or be coupled to or formed by a portion of the second conductor 118. In some embodiments, the negative electrode can be provided via one or more external electrodes, such as a needle puncturing the patient, or a grounding pad applied to the patient's skin; in some such embodiments, or otherwise, the first conductor 116 or the second conductor 118 may be omitted from the core assembly 105.

The system can include multiple (e.g., two or more), distinct conductive paths or channels for passing electrical current along the system. The interventional element 106 can serve as one electrode (e.g., a positive electrode) in electrical communication with a conductive path via the first conductor 116. Another of the conductive paths of the system can be in electrical communication with another electrode (e.g., a negative electrode). For example, the second conductor 118 can serve as the second conductive path, with one or more uninsulated portions of the second conductor 118 forming the negative electrode(s).

Figure 1B:
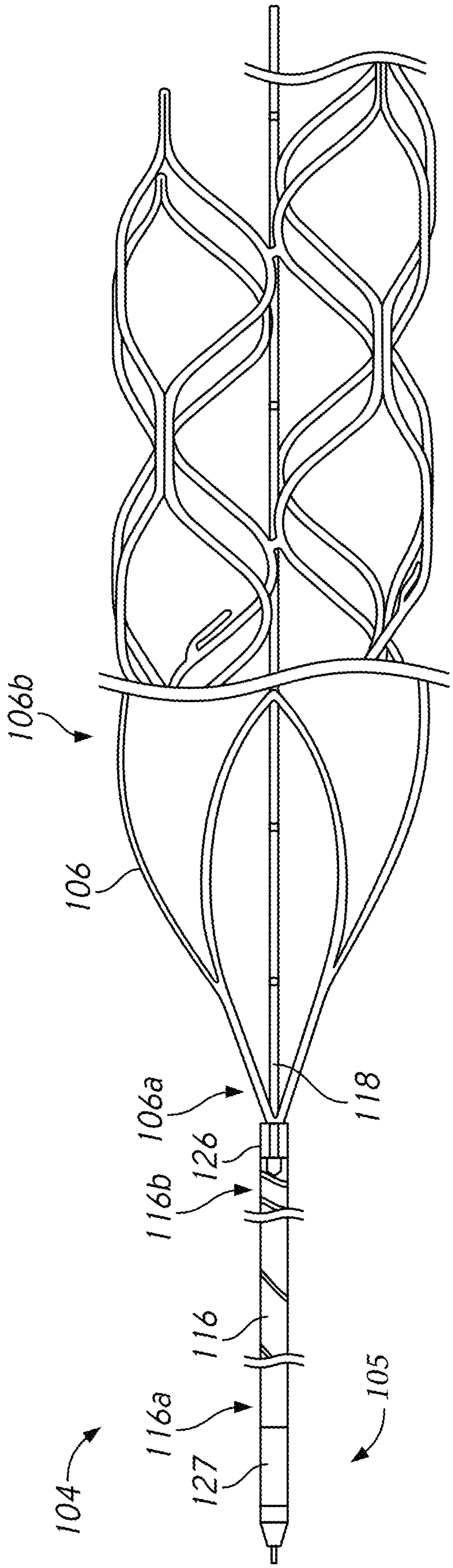
FIG. 1B shows a side schematic view of the treatment device for retrieving material from a body lumen, in accordance with one or more embodiments of the present technology.

As shown in FIG. 1B, the first conductor 116 and the interventional element 106 can be joined at a connection 126 to secure the interventional element 106 relative to the first conductor 116 and to complete an electrical pathway between the elongate first conductor 116 and the interventional element 106. As illustrated in FIG. 1B, the distal end portion of the second conductor 118 is configured to be positioned distal of the distal end portion of the first conductor 116. The interventional element 106 can be metallic or otherwise electrically conductive so that when the interventional element 106 is placed in the presence of blood (or thrombus, and/or any other electrolytic medium which may be present, such as saline) and voltage is applied via the electrical connectors of the current generator 102, current flows from the positive connector of the current generator 102, distally along the first conductor 116 to the interventional element 106 and through the surrounding media (e.g., blood, tissue, thrombus, etc.) before returning proximally along the second conductor 118 to the negative electrical connector of the current generator 102, thereby positively charging at least a portion of the interventional element 106 and promoting clot adhesion.

In certain embodiments, the polarities of the current generator 102 can be switched, so that the negative electrical connector is electrically coupled to the first conductor 116 and the positive electrical connector is electrically coupled to the second conductor 118. This can be advantageous when, for example, attempting to attract predominantly positively charged material to the interventional element 106, or when attempting to break up a clot rather than grasp it with an interventional element 106. In some embodiments alternating current (AC) signals may be used rather than DC. In certain instances, AC signals may advantageously help break apart a thrombus or other material.

In various embodiments, the interventional element 106 can take any number of forms, for example a removal device, a thrombectomy device, or other suitable medical device. For example, in some embodiments the interventional element 106 may be a stent and/or stent retriever, such as Medtronic's Solitaire™ Revascularization Device, Stryker Neurovascular's Trevo® ProVue™ Stentriever, or other suitable devices. In some embodiments, the interventional element 106 may be a coiled wire, a weave, and/or a braid formed of a plurality of braided filaments. Examples of suitable interventional elements 106 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The interventional element 106 can have a low-profile, constrained or compressed configuration for intravascular delivery to the treatment site within the third catheter 114, and an expanded configuration for securing and/or engaging clot material and/or for restoring blood flow at the treatment site. The interventional element 106 has a proximal portion including an attachment portion **106*a* that may be coupled to the first conductor 116 and a distal portion comprising an open cell framework or body 106*b*. In some embodiments, the body 106*b* of the interventional element 106 can be generally tubular (e.g., cylindrical), and the proximal portion of the interventional element 106 can taper proximally to the attachment portion 106*a*. In various embodiments, the interventional element 106 can define a lumen that is located radially inward from the body 106*b***.

The interventional element 106 can be a metallic and/or electrically conductive thrombectomy device. For example, the interventional element can include or be made of stainless steel, nitinol, cobalt-chromium, platinum, tantalum, alloys thereof, or any other suitable material. In some embodiments, the interventional element 106 is a mesh structure (e.g., a braid, a stent, etc.) formed of a superelastic material (e.g., Nitinol) or other resilient or self-expanding material configured to self-expand when released from the third catheter 114. The mesh structure may include a plurality of struts and open spaces between the struts. In some embodiments, the struts and spaces may be situated along the longitudinal direction of the interventional element 106, the radial direction, or both.

In some embodiments, the first conductor 116 can be a structural element configured to push and pull a device such as the interventional element 106 along the bodily lumen. The first conductor 116 can be any suitable elongate member configured to advance the interventional element 106 to a treatment site within a blood vessel. For example, the first conductor 116 can be or include a wire, tube (e.g., a hypotube), coil, or any combination thereof. According to some embodiments, the first conductor 116 comprises an elongate tubular member defining a lumen therethrough. In some embodiments, the first conductor 116 can comprise a distally located aperture configured to receive the attachment portion of the interventional element. In some embodiments, the first conductor 116 comprises a distally located joining element comprising the aperture configured to receive the attachment portion. The first conductor 116 can have a length sufficient to extend from a location outside the patient's body through the vasculature to a treatment site within the patient's body. The first conductor 116 can be a monolithic structure or formed of multiple joined segments. In some embodiments, the first conductor 116 can comprise a laser-cut hypotube having a spiral cut pattern (or other pattern of cut voids) formed in its sidewall along at least a portion of its length. The first conductor 116 can be metallic and/or otherwise electrically conductive to deliver current from the current generator 102 to the interventional element 106. For example, the first conductor 116 can comprise or consist of nickel titanium alloy, stainless steel, or other metals or alloys. In embodiments that comprise multiple joined segments, the segments may be of the same or different materials. For example, some or all of the first conductor 116 can be formed of stainless steel, or other suitable materials known to those skilled in the art. Nickel titanium alloy may be preferable for kink resistance and reduction of imaging artifacts.

In some embodiments, the second conductor 118 can be a structural element configured to secure or retain a position of the interventional element 106 relative to the first conductor 116. Additionally, or alternatively, the second conductor 118 can be configured to be a negative electrode. The second conductor 118 can be any suitable elongate member configured to extend through a lumen of the first conductor 116. For example, the second conductor 118 can be or include a wire, tube (e.g., a hypotube), coil, or any combination thereof. The second conductor 118 can have a length sufficient to extend from a location outside the patient's body through the vasculature to a treatment site within the patient's body. The second conductor 118 can be a monolithic structure or formed of multiple joined segments. The second conductor 118 can be metallic or electrically conductive to deliver current from the surrounding media (e.g., blood, tissue, thrombus, etc.) to the current generator 200. For example, the second conductor 118 can comprise or consist of nickel titanium alloy, stainless steel, or other metals or alloys. In embodiments that comprise multiple joined segments, the segments may be of the same or different materials. For example, some or all of the second conductor 118 can be formed of stainless steel, or other suitable materials known to those skilled in the art. Nickel titanium alloy may be preferable for kink resistance and reduction of imaging artifacts. The second conductor 118 can be electrically insulated along some or all of its length. In some embodiments, the second conductor 118 comprises an insulated wire or guide wire having one or more exposed, electrically conductive portions. For example, a distal end portion of the second conductor 118 can be exposed to conduct current from surrounding media (e.g., blood, tissue, thrombus, etc.) at a treatment site.

In some embodiments, the treatment device 104 can comprise one or more electrically insulating materials. For example, an insulating material can be disposed on one or more portions of the second conductor 118 to electrically isolate the second conductor 118 from the first conductor 116, the connection 126, and/or the interventional element 106. Additionally or alternatively, an insulating material can be disposed within a lumen of the first conductor 116 to electrically isolate the first conductor 116 from the second conductor 118 and/or the attachment portion of the interventional element 106. In some embodiments, an insulating material is disposed over an outer surface of the first conductor 116 along at least a portion of a length of the first conductor 116 to direct current through the first conductor 116 and prevent current loss from the first conductor 116 to the surrounding environment. As shown in FIG. 1B, in some embodiments, an insulating material 127 can be disposed adjacent to a proximal end portion **116*a* and/or a distal end portion 116*b* of the first conductor 116. The insulating material 127 may be disposed along an entire length of the first conductor 116 and/or the second conductor 118 or the insulating material may be disposed along select portions of the first conductor 116 and/or the second conductor 118. The insulating material 127** may comprise a polymer, such as polyimide, parylene, PTFE, or another suitable electrically insulating material.

Figure 1C:
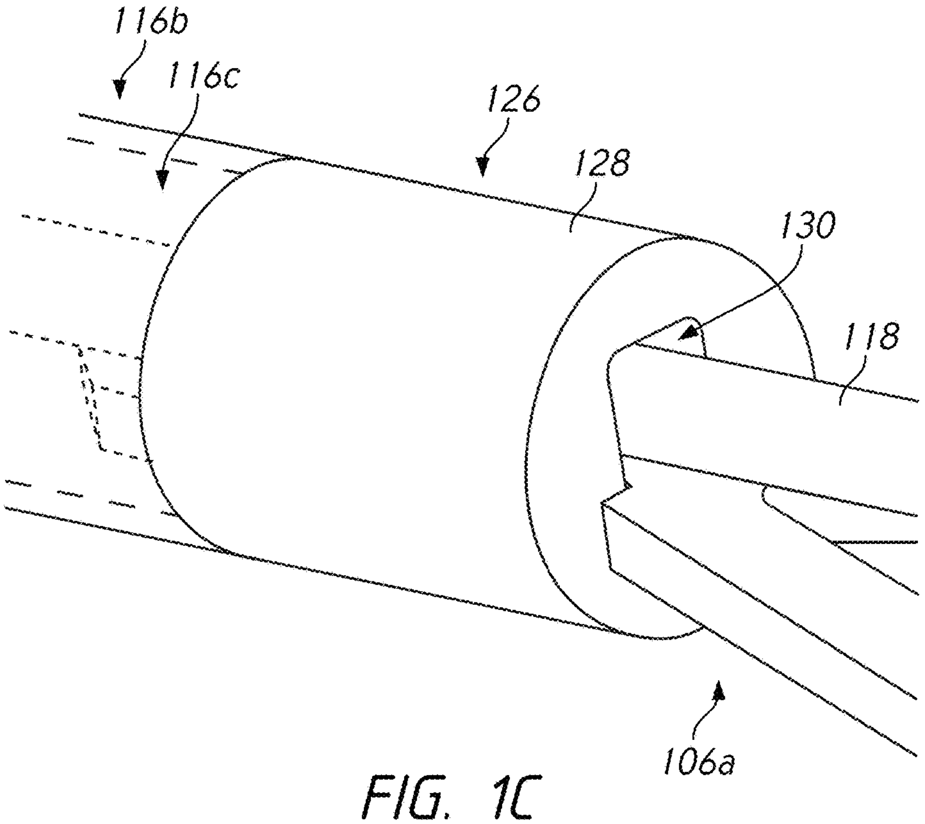
FIG. 1C shows an isometric view of an interventional element and an elongate member positioned within a joining element in accordance with one or more embodiments of the present technology.

As shown in FIGS. 1B and 1C, the interventional element 106 and the first conductor 116 can be coupled at a connection 126. According to some embodiments, the interventional element 106 and the first conductor 116 can be substantially permanently attached together at the connection 126. That is, the interventional element 106 and the first conductor 116 can be attached together in a manner that, under the expected use conditions of the device, the interventional element 106 and the first conductor 116 would not become unintentionally separated from one another. In some embodiments, the treatment device 104 can comprise a portion, located proximally or distally of the connection 126, that is configured for selective detachment of the interventional element 106 from the first conductor 116. For example, such a portion can comprise an electrolytically severable segment of the first conductor 116. In some embodiments, the device can be devoid of any feature that would permit selective detachment of the interventional element 106 from the first conductor 116. The connection 126 can provide a mechanical interlock between the interventional element 106 and the first conductor 116. Moreover, the connection 126 can be configured to complete an electrically conductive path between the interventional element 106 and the elongate first conductor 116.

FIG. 1C illustrates an enlarged perspective view of the connection 126, according to some embodiments, between the first conductor 116 and the interventional element 106. In some embodiments, for example as shown in FIG. 1C, the first conductor 116 comprises a distally located joining element 128 including an aperture 130 configured to receive a proximally located attachment portion **106*a* of the interventional element 106 and/or at least a portion of the second conductor 118. As shown in FIG. 1C, the attachment portion 106*a* of the interventional element 106 is configured to mechanically interlock with a joining element 128 to secure the interventional element 106 to the core assembly 105. In some embodiments, the second conductor 118 can be disposed within the aperture at a radially adjacent position relative to the attachment portion 106***a* to facilitate such securement. Further, the second conductor 118 may be affixed to the joining element 128 via a weld, an adhesive, a threaded connection, an interference fit, or any other suitable connection.

In some embodiments, the connection 126 can comprise a bonding agent in addition or alternative to the joining element 128 and/or second conductor 118. The bonding agent can comprise adhesive, solder, welding flux, brazing filler, etc., disposed within the joining element 128, and/or adjacent to it, just proximal of and/or just distal of the joining element 128. In some embodiments, the bonding agent can bond to the connection 126 without applying heat. For example, the bonding agent can comprise a UV-curable adhesive. In embodiments that comprise a polymer coating of the wire or polymer tubing, use of a bonding agent that avoids application of heat that would damage the polymer may be preferred.

In some embodiments, the connection 126 can comprise a locking element. The locking element can be coupled with the joining element 128 and can be configured to inhibit motion of the attachment portion 106*a*. Examples of suitable locking elements can include any of the disclosed locking elements in U.S. Provisional Application No. 63/199,352 filed Dec. 21, 2020, which is hereby incorporated by reference in its entirety.

Figure 2:
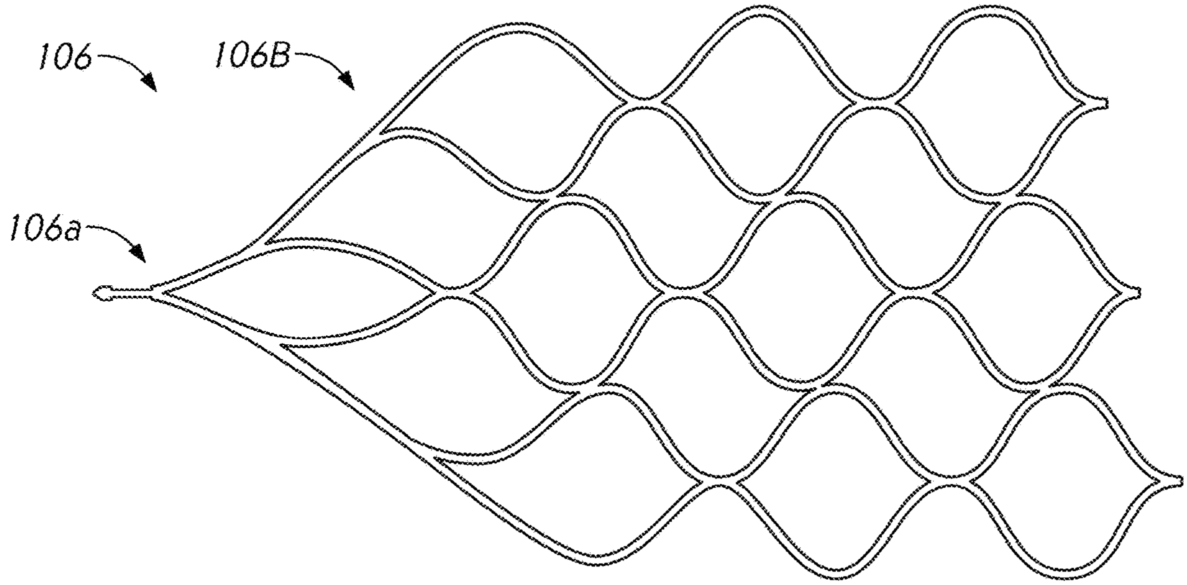
FIG. 2 shows a plan view of an interventional element in an unfurled configuration in accordance with one or more embodiments of the present technology.

FIG. 2 is a plan view of the interventional element 106, depicted in an unfurled or flattened configuration for ease of understanding. The interventional element 106 has a proximal portion that may be coupled to the first conductor 116 and a distal portion. The interventional element 106 has a proximal portion including an attachment portion 106*a* that may be coupled to the first conductor 116 and a distal portion comprising an open cell framework or body 106*b*. The attachment portion 106*a* of the interventional element 106 can have a substantially constant thickness, such as would result from the interventional element 106 being cut from a tube or sheet of material, for example. In other embodiments, the thickness of the attachment portion 106*a* can vary across its length, width, or both.

Figure 3:
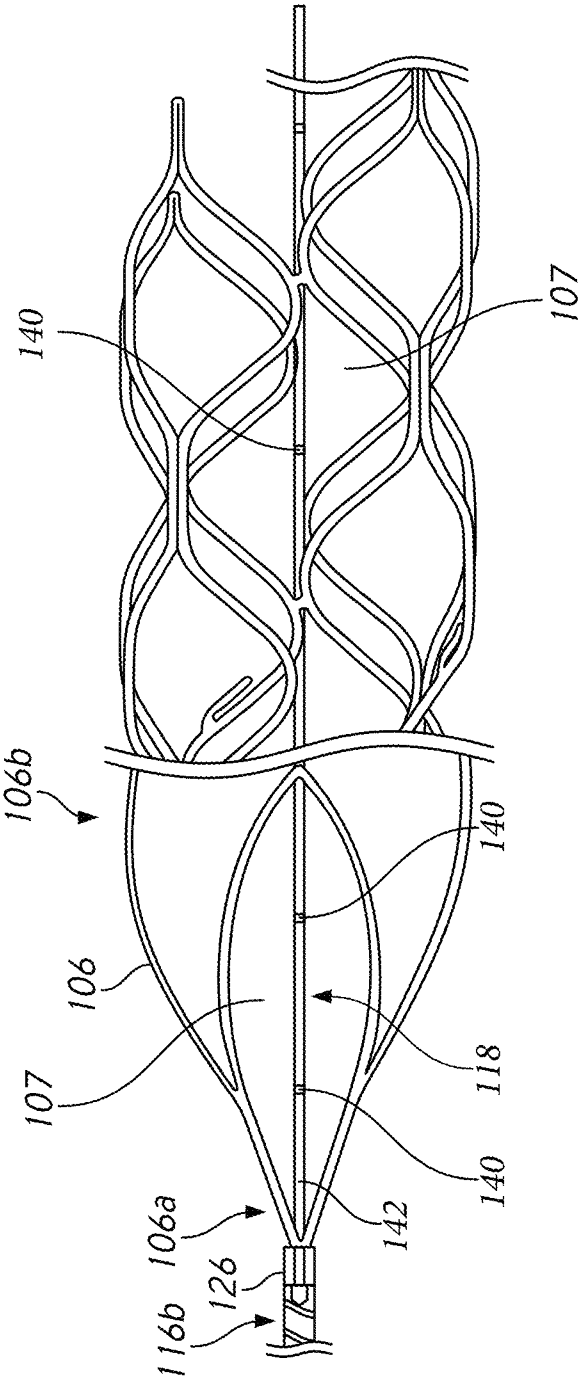
FIG. 3 shows a side schematic view of the treatment device for retrieving material from a body lumen, in accordance with one or more embodiments of the present technology.

FIG. 3 illustrates a side schematic view of a portion of the treatment device 104. As illustrated in FIG. 3, the interventional element 106 extends distally from the first conductor 116. As noted previously, the interventional element 106 can be in electrical communication with the first conductor 116, such that current supplied to a proximal end of the first conductor 116 is carried through the first conductor 116 to the interventional element 106. The second conductor 118 can extend through the lumen of the first conductor 116 and beyond a distal end of the first conductor 116, such that a distal portion of the second conductor 118 extends through an interior region of the interventional element 106. As noted previously, the second conductor 118 can be covered with an electrically insulative material 142 along at least a portion of its length. At one or more positions along a distal region of the second conductor 118, the insulative material 142 can form gaps or apertures that each define an electrode portion 140 formed by the exposed conductive metal of the underlying second conductor 118. In operation, current can flow from the interventional element 106, through surrounding media (e.g., blood, saline, etc.), to the electrode portions 140, and along the second conductor 118 to return to the current generator.

The second conductor 118 can include an insulative material 142 that surrounds the second conductor 118 and which has several openings formed within the insulative material 142. These openings can define electrode portions 140. The insulative material 142 can be the same, or similar to, the insulative material 127. Accordingly, the portions of the second conductor 118 that are surrounded by the insulative material 142 can be electrically isolated from other components, while the openings formed within the insulative material 142 can provide electrical access to the second conductor 118 at the openings. In some embodiments, the electrode portions 140 include a coating or other conductive element that is applied over the surface of the second conductor 118.

In various embodiments, the insulative material 142 can define the electrode portions 140. For example, as illustrated in FIG. 3, the electrode portions 140 can be defined by the regions of the second conductor 118 that are uncovered by the insulative material 142. In some embodiments, the electrode portions 140 can be defined by the portions of the second conductor 118 that are uncovered by the insulative material 142 and any intervening insulative material 142 between the uncovered portions of the second conductor. In various embodiments, the treatment device 104 can include one or more electrode portions 140 at or near the distal end of the second conductor 118. In some embodiments, the electrode portions 140 can take the form of one or more discrete electrodes coupled to the second conductor 118.

As illustrated in FIG. 3, the electrode portions 140 of the second conductor 118 can be disposed radially adjacent to or distal of interventional element 106. For example, the electrode portions 140 can be disposed distally of the connection 126 and be positioned radially inward of the interventional element 106. In some embodiments, one or more electrode portions 140 extend (or are positioned) distally of the distal end of the interventional element 106. In various embodiments, the second conductor 118 and electrode portions 140 are disposed within the lumen of the interventional element 106. In some embodiments, the openings formed within the insulating material 142 (and/or the electrode portions 140) can be disposed proximate or radially adjacent to the spaces or cell openings 107 bounded by the struts of the body 106*b* of the interventional element 106. In some embodiments, each of the electrode portions 140 of the second conductor 118 is positioned radially adjacent to a cell opening 107 of the interventional element 106, and/or each portion of the second conductor 118 that is radially adjacent to a strut (and/or other metallic component, such as a radiopaque marker) of the interventional element 106 is insulated.

FIGS. 4-7 illustrate several schematic views of the second conductor 118, according to one or more embodiments of the present technology. In some embodiments, an insulative material 142 can couple to the second conductor 118. For example, the insulative material 142 can couple to the outer surface of the second conductor 118. In various embodiments, the insulative material 142 surrounds the second conductor 118. In some embodiments, the insulating material 142 can extend along at least a portion of the length of second conductor 118. In some embodiments, the insulating material 142 can extend from a proximal end portion 118*a* of the second conductor 118 to a distal end portion 118*b* of the second conductor 118. The insulating material 142 may comprise a polymer, such as polyimide, parylene, PTFE, or another suitable electrically insulating material.

Figure 4:
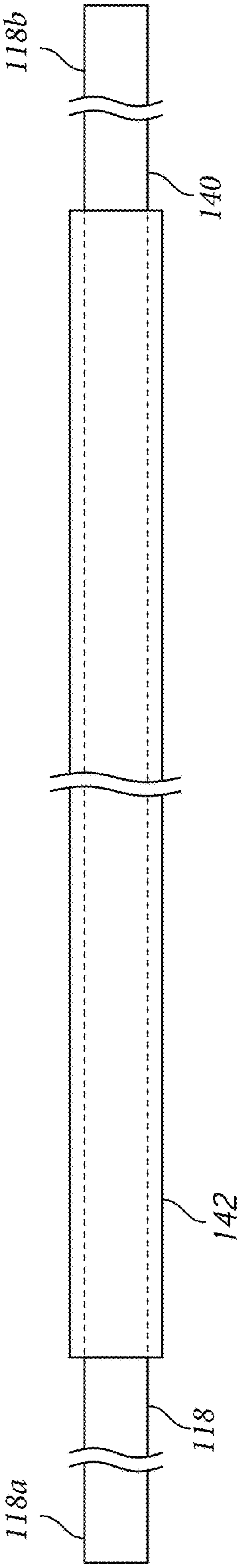
FIG. 4 shows a side schematic view of a conductor in accordance with one or more embodiments of the present technology.

As previously discussed, the insulating material 142 can define one or more electrode portions 140 of the second conductor 118. The electrode portions 140 can include one or more uninsulated portions of the second conductor 118 that allow for the second conductor 118 to electrically couple to other components via, e.g., surrounding media such as thrombus, blood, saline, tissue, etc. For example, as illustrated in FIG. 4, the distal end 118*b* of the second conductor 118 can be uninsulated, allowing for that portion of the second conductor 118 to electrically couple to other components or media. The electrode portions 140 can be disposed along one or more locations of the second conductor 118. For example, one or more electrode portions 140 can be spaced apart from a distal terminus 118*b* of the second conductor 118 by a portion of the insulative material 142.

Figure 5:
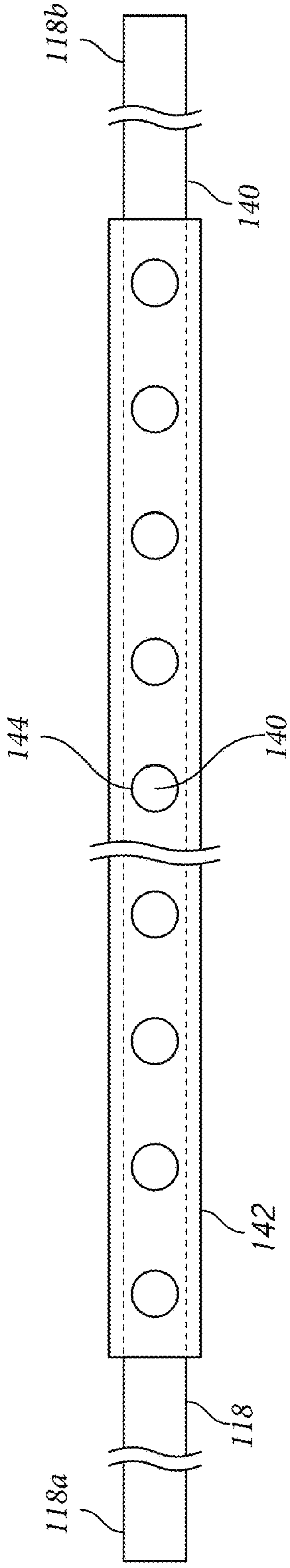
FIG. 5 shows a side schematic view of a conductor in accordance with one or more embodiments of the present technology.
Figure 6:
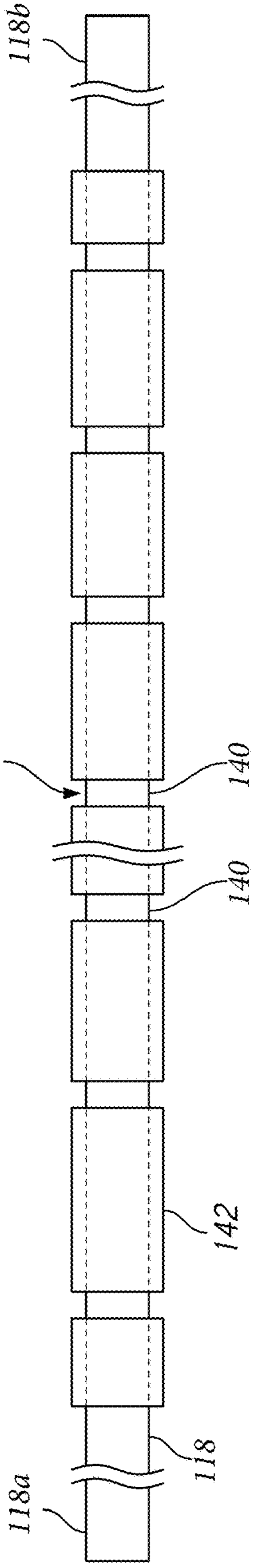
FIG. 6 shows a side schematic view of a conductor in accordance with one or more embodiments of the present technology.

In various embodiments, the electrode portions 140 can include one or more openings 144 formed into the insulating material 142. For example, as illustrated in FIG. 5, multiple openings 144 can be formed along the length of the insulating material 142. The openings 144 can expose a portion of the second conductor 118 and allow for the second conductor 118 to electrically couple with another component or media. The openings 144 can be spaced apart along the length of insulating material 142. In some embodiments, the openings 144 are evenly spaced along the length of the insulating material 142. In various embodiments, the openings 144 are unevenly spaced along the length of the insulating material 142. For example, in some embodiments, more openings 144 can be formed near the distal end of the insulating material 142 than the proximal end of the insulating material 142. In various embodiments, the openings 144 can take the form of one or more shapes, including circular, elliptical, regular polygonal, irregular polygonal, triangular, square, rectangular, pentagonal, hexagonal, or any other suitable shape. As illustrated in FIG. 5, some or all of the electrode portions 140/openings 144 can be located at the same angular position about the longitudinal axis of the second conductor 118, e.g. at the "twelve o'clock" position on the second conductor. When all of the portions 140/openings 144 are at such a common angular position, that angular position can be oriented to face away from the portion of the interventional element 106 which is nearest to the second conductor 118 (and/or to face radially inward toward the lumen or longitudinal axis of the interventional element). Such an orientation helps minimize the risk of electrical shorts arising from inadvertent contact of the electrode portions 140 with the struts of the interventional element. Furthermore, such an arrangement and orientation of the portions 140/openings 144 can be combined with the alignment of the electrode portions 140 with the cell openings 107 described herein with respect to FIG. 3.

In various embodiments, the electrode portions 140 can include one or more annular openings 146 formed into the insulating material 142. For example, as illustrated in FIG. 5, multiple annular openings 146 can be formed along the length of the insulating material 142. The annular openings 146 can be formed around a part or all of the circumference of the insulating material 142, which can expose a portion of the second conductor 118 and allow for the second conductor 118 to electrically couple with another component or media. The annular openings 146 can be spaced apart along the length of insulating material 142. In some embodiments, the annular openings 146 are evenly spaced along the length of the insulating material 142. In various embodiments, the annular openings 146 are unevenly space along the insulating material 142. For example, in some embodiments, more annular openings 146 can be formed near the distal end of the second conductor 118 than at a more proximal position of the second conductor 118.

Figure 7:
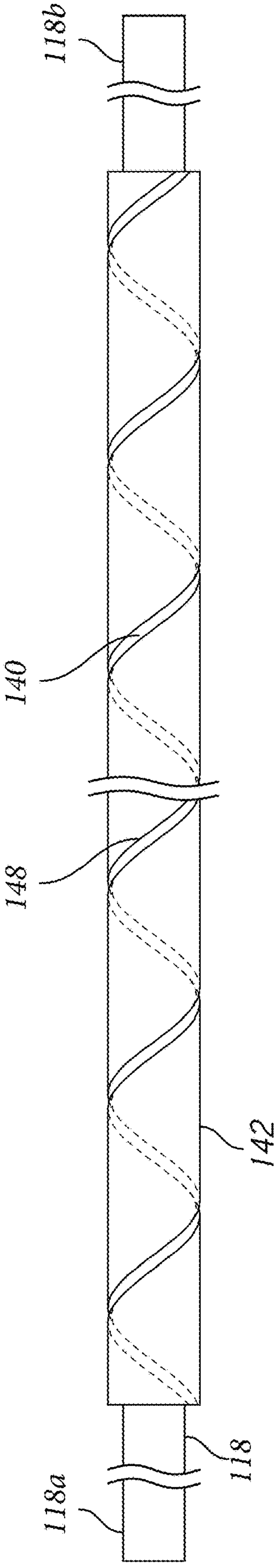
FIG. 7 shows a side schematic view of a conductor in accordance with one or more embodiments of the present technology.

In various embodiments, the electrode portions 140 can include one or more spiral or helical openings 148 formed into the insulating material 142. For example, as illustrated in FIG. 7, a spiral opening 148 can be formed along the length of the insulating material 142. The spiral openings 148 can form an opening that wraps around at least a portion of the insulating material 142 as it extends longitudinally or distally. The spiral openings 148 can expose a portion of the second conductor 118 and allow for the second conductor 118 to electrically couple with another component or media.

In some embodiments, the electrode portions 140 can include a combination of openings formed in the insulating material 142. For example, in some embodiments, the electrode portions 140 can include one or more openings 144, one or more annular openings 146, and/or one or more spiral openings 148. In some embodiments, the electrode portion 140 can take the form of an uninsulated distal terminus 118*b* of the second conductor 118; such an electrode portion can be employed instead of or in addition to other electrode portion(s) 140 located along the length of the second conductor 118 proximal of the distal terminus 118*b*.

In some embodiments, some or all of the electrode portions 140 can include the same material as a part of the interventional element 106. For example, the uninsulated material of the second conductor 118 within the electrode portion 140 can be the same material as the interventional element 106. In some embodiments, the interventional element 106 is coated, plated or surface-treated with an outer layer of electrically conductive material, which can be the same material as the uninsulated portions of the second conductor 118.

In some embodiments, components of the treatment device 104 can electrically couple to the second conductor 118 through the electrode portions 140 (e.g. via surrounding media). Because the second conductor 118 is not electrically isolated completely at the electrode portions 140, the second conductor 118 can electrically couple to other components at the electrode portions 140. For example, in some embodiments, the interventional element 106 can couple to the second conductor 118 through the electrode portions 140. In various embodiments, the electrode portions 140 can be used to complete a circuit between the first conductor 116 and second conductor 118. For example, the current generator 102 can couple to the core assembly 105 at the proximal portion 104*a* of the treatment device 104 and send a current through the first conductor 116. This current can flow through the first conductor 116 to the interventional element 106. At the interventional element 106, the current can flow through the patient's surrounding media (e.g., blood, tissue, saline, thrombus, etc.) to the electrode portions 140 of the second conductor 118, where the current can then flow through the second conductor 118 and return to the current generator 102.

In various embodiments, the electrode portions 140 can be configured to prevent the circuit between the first conductor 116 and second conductor 118 from shorting. For example, by positioning the electrode portions 140 distally from the attachment portion 106*a* of the interventional element 106, the electrode portions 140 can prevent the circuit from shorting at proximate the attachment portion 106*a*. Additionally, in some embodiments, positioning the uninsulated portions of the second conductor 118 so that the uninsulated portions are proximate or radially adjacent to the spaces or cell openings 107 defined by the body 106*b* (e.g. by the struts thereof) can also prevent the circuit from shorting. In some embodiments, the electrode portions 140 can be configured to allow for the interventional element

106 to maintain a desirable electrical charge distribution. For example, positioning the electrode portions 140 proximate the distal terminus 118*b* of the second conductor 118 encourages the more current to flow through the distal portions of the interventional element 106 to reach the electrode portions 140, which in turn allows for the interventional element 106 to maintain a favorable electrical charge distribution (e.g., with sufficiently high charge density at the distal region of the interventional element, along the working length of the interventional element, or other suitable charge distribution). In some embodiments, spacing the openings (e.g. openings 144, annular openings 146, and/or spiral openings 148) of the electrode portions apart along the length of second conductor 118 can also allow for the interventional element 106 to maintain an electrical charge.

An example method of delivering a current to the treatment device 104 will now be described. First, the treatment device 104 is positioned within a patient at the treatment site. Once the treatment device 104 is properly positioned, the user can expand the interventional element 106 so that the interventional element 106 engages with the thrombus. After the interventional element 106 engages with the thrombus, the user can couple the core assembly 105 to the current generator 102. In some embodiments, the core assembly 105 is previously coupled to the current generator 102. The user can interact with current generator to initiate the supply of an electrical signal to the first conductor 116. The electrical signal can travel toward the treatment site through the first conductor 116 and to the interventional element 106. The electrical signal can return to the current generator 102 by flowing from the interventional element, through the surrounding media (e.g., blood, tissue, thrombus, etc.) to the electrode portions 140 of the second conductor 118 and through the second conductor 118 to the current generator 102. In some embodiments, the electrical signal is an electrical current of between about 0-5 mA. The electrical signal can be unipolar (e.g., DC) or bipolar (e.g., AC). In various embodiments, the current or voltage level of the electrical signal can be constant, periodic, irregular, or any combination thereof. In some embodiments, the electrical signal is supplied for a duration of time between about 30 seconds to about 10 minutes. In some embodiments, the electrical signal is supplied for a duration of time of two minutes or less. After the electrical signal is delivered to the treatment device 104 for the proper duration, the user can interact with current generator to stop the supply of the electrical signal. The user can then proximally retract the treatment device 104, including the thrombus, into a surrounding catheter, and then remove the entire assembly from the patient.

CONCLUSION

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A medical device comprising:

a stent having an expanded configuration in which the stent is released into a blood vessel and a compressed configuration in which the stent is housed within a microcatheter during delivery of the stent to a treatment site, wherein the stent has a cylindrical body; and a guide wire coupled to the stent, wherein the guide wire has at least one connection point with a tube through which the guide wire runs, and wherein the guide wire extends beyond a distal end of the stent.

2. The medical device of claim 1, wherein the at least one connection point between the stent and the guide wire includes a locking element, wherein the locking element is configured to inhibit motion of a proximal portion of the stent.

3. The medical device of claim 1, wherein the stent and the guide wire are non-slidably coupled together.

4. The medical device of claim 1, wherein the stent and the guide wire are coupled via an interference fit.

5. The medical device of claim 1, wherein the stent has at least two connection points with the guide wire.

6. The medical device of claim 1, wherein the guide wire is disposed radially adjacent to the stent.

7. The medical device of claim 1, wherein the guide wire is welded to the stent.

8. A medical device comprising:

a stent having an expanded configuration in which the stent is released in a blood vessel and a compressed configuration in which the stent is housed within a microcatheter during delivery of the stent to a treatment site, wherein the stent has a cylindrical body, and wherein the stent has a connection point with a tube through which a guide wire runs, the guide wire configured to be positioned distally beyond the stent.

9. The medical device of claim 8, wherein the guide wire is disposed radially adjacent to the stent.

10. The medical device of claim 8, wherein the tube is made of a metal.

11. The medical device of claim 8, wherein the tube comprises a plurality of cuts in one or more sidewalls of the tube.

12. The medical device of claim 8, wherein the stent has a tapered proximal portion proximal to the cylindrical body, the tapered proximal portion tapering to the connection point.

13. The medical device of claim 8, wherein the guide wire comprises a plurality of joined segments, wherein the joined segments include different materials.

14. The medical device of claim 8, wherein the stent further comprises a radiopaque marker.

15. The medical device of claim 8, wherein the stent is self-expandable, and wherein the stent is configured to self-expand when released by the microcatheter.

16. The medical device of claim 8, wherein the medical device is configured to remove a thrombus from the blood vessel.

17. The medical device of claim 8, wherein the stent is configured to restore blood flow at the treatment site.

18. The medical device of claim 8, wherein the connection point between the stent and the guide wire is electrolytically or mechanically severable.

19. The medical device of claim 8, wherein the guide wire extends distally beyond the microcatheter.

20. A method comprising:

introducing a medical device into a blood vessel, wherein the medical device comprises an expandable stent having a cylindrical body, the expandable stent having a connection point with a tube through which a guide wire runs, the guide wire configured to be positioned distally beyond the stent; and distally advancing a microcatheter together with the guide wire distally.

* * * * *